(12) United States Patent
Shao et al.

(10) Patent No.: US 9,765,015 B2
(45) Date of Patent: Sep. 19, 2017

(54) BRANCHED POLYOL ADDITIVES FOR ELECTROPHORETIC MEDIA

(71) Applicant: E INK CALIFORNIA, LLC, Fremont, CA (US)

(72) Inventors: Lin Shao, Fremont, CA (US); Haiyan Gu, Fremont, CA (US); Vladimir Sofiyev, Oakland, CA (US); Ming Wang, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 0 days.

(21) Appl. No.: 15/403,370

(22) Filed: Jan. 11, 2017

(65) Prior Publication Data
US 2017/0204047 A1 Jul. 20, 2017

Related U.S. Application Data

(60) Provisional application No. 62/279,822, filed on Jan. 17, 2016.

(51) Int. Cl.
| | | |
|---|---|---|
| *G02B 5/23* | (2006.01) | |
| *C07C 69/34* | (2006.01) | |
| *C07C 69/33* | (2006.01) | |
| *G02F 1/167* | (2006.01) | |
| *G09G 3/34* | (2006.01) | |
| *G02B 26/00* | (2006.01) | |

(52) U.S. Cl.
CPC .............. *C07C 69/34* (2013.01); *C07C 69/33* (2013.01); *G02F 1/167* (2013.01); *G02F 2001/1678* (2013.01)

(58) Field of Classification Search
CPC ......... C07C 69/34; C07C 69/33; G02F 1/167; G02F 2001/1678
USPC .......... 252/586; 345/107; 359/296; 427/490, 427/496, 500
See application file for complete search history.

(56) References Cited

U.S. PATENT DOCUMENTS

| | | | |
|---|---|---|---|
| 2,800,457 | A | 7/1957 | Green et al. |
| 4,001,140 | A | 1/1977 | Foris |
| 4,273,672 | A | 6/1981 | Vassiliades |
| 4,522,908 | A | 6/1985 | De Winter et al. |
| 6,327,072 | B1 | 12/2001 | Comiskey |
| 6,672,921 | B1 | 1/2004 | Liang |
| 6,788,449 | B2 | 9/2004 | Liang |
| 6,866,760 | B2 | 3/2005 | Paolini, Jr. |
| 6,930,818 | B1 | 8/2005 | Liang |
| 6,982,178 | B2 | 1/2006 | LeCain |
| 7,170,670 | B2 | 1/2007 | Webber |
| 7,205,355 | B2 | 4/2007 | Liang |
| 7,224,511 | B2 | 5/2007 | Takagi |
| 7,236,290 | B1 | 6/2007 | Zhang et al. |
| 7,236,291 | B2 | 6/2007 | Kaga |
| 7,321,459 | B2 | 1/2008 | Masuda |
| 7,339,715 | B2 | 3/2008 | Webber et al. |
| 7,405,865 | B2 | 7/2008 | Ogiwara |
| 7,411,719 | B2 | 8/2008 | Paolini, Jr. et al. |
| 7,715,087 | B2 | 5/2010 | Hou |
| 7,736,829 | B2 | 6/2010 | Silcoff |
| 8,625,188 | B2 | 1/2014 | Wang |
| 8,717,664 | B2 | 5/2014 | Wang |
| 8,902,491 | B2 | 12/2014 | Wang |
| 9,039,938 | B2 | 5/2015 | Crain |
| 9,052,564 | B2 | 6/2015 | Sprague |
| 9,081,250 | B2 | 7/2015 | Liang |
| 9,223,164 | B2 | 12/2015 | Lai |
| 9,337,737 | B2 | 5/2016 | Yang et al. |
| 9,512,320 | B2 | 12/2016 | Denda et al. |
| 2010/0290103 | A1 | 11/2010 | Fontana |
| 2012/0118198 | A1 | 5/2012 | Zhou |
| 2014/0364548 | A1 | 12/2014 | Everhardus |
| 2015/0005720 | A1 | 1/2015 | Zang |
| 2015/0213765 | A1 | 7/2015 | Gates |
| 2015/0378235 | A1 | 12/2015 | Lin |
| 2016/0109780 | A1 | 4/2016 | Liu |

FOREIGN PATENT DOCUMENTS

JP 2006313334 11/2006

OTHER PUBLICATIONS

Kitamura, T. et al., "Electrical toner movement for electronic paper-like display", Asia Display/IDW '01, p. 1517, Paper HCS1-1 (2001) Jan. 1, 2001.
Yamaguchi, Y. et al., "Toner display using insulative particles charged triboelectrically", Asia Display/IDW '01, p. 1729, Paper AMD4-4 (2001) Jan. 1, 2001.
Korean Intellectual Property Office; PCT/US2017/012951; International Search Report and Written Opinion; dated Apr. 19, 2017. Apr. 19, 2017.
Korean Intellectual Property Office; PCT/US2017/012911; International Search Report and Written Opinion; dated Apr. 27, 2017. Apr. 27, 2017.
Korean Intellectual Property Office; PCT/US2017/012926; International Search Report and Written Opinion; dated May 1, 2017. May 1, 2017.

*Primary Examiner* — Bijan Ahvazi
(74) *Attorney, Agent, or Firm* — Brian D. Bean

(57) ABSTRACT

Additives for electrophoretic media comprising esters of branched polyols and fatty acids, such as esters of pentaerythritol propoxylate (5/4 PO/OH) and stearic acid. The fatty acids may be saturated or unsaturated, branched or unbranched. In some embodiments, the fatty acids are perfluorinated, or partially fluorinated. In some embodiments, the branched polyol will include oligomers of polypropylene oxide or polyethylene oxide. When the additives are included in an electrophoretic medium in a display, the resulting display has an improved contrast ratio and reducing ghosting.

26 Claims, No Drawings

BRANCHED POLYOL ADDITIVES FOR ELECTROPHORETIC MEDIA

RELATED APPLICATIONS

This application claims priority to U.S. provisional application No. 62/279,822, filed Jan. 17, 2016, which is incorporated herein by reference in its entirety.

BACKGROUND OF INVENTION

This invention relates to electrophoretic displays and additives that interact with pigments included in electrophoretic media to improve the performance of the media when used in a display. For example, the additives of the invention can improve the contrast between light (on) and dark (off) states for a variety of pigments. The additives also diminish images that remain after a display has been switched between images, a phenomenon known as "ghosting."

Particle-based electrophoretic displays have been the subject of intense research and development for a number of years. In such displays, a plurality of charged particles (sometimes referred to as pigment particles) move through a fluid under the influence of an electric field. The electric field is typically provided by a conductive film or a transistor, such as a field-effect transistor. Electrophoretic displays have good brightness and contrast, wide viewing angles, state bistability, and low power consumption when compared with liquid crystal displays. Such electrophoretic displays have slower switching speeds than LCD displays, however, and electrophoretic displays are typically too slow to display real-time video. Additionally, the electrophoretic displays can be sluggish at low temperatures because the viscosity of the fluid limits the movement of the electrophoretic particles. Despite these shortcomings, electrophoretic displays can be found in everyday products such as electronic books (e-readers), mobile phones and mobile phone covers, smart cards, signs, watches, shelf labels, and flash drives.

An electrophoretic image display (EPID) typically comprises a pair of spaced-apart plate-like electrodes. At least one of the electrode plates, typically on the viewing side, is transparent. An electrophoretic fluid composed of a dielectric solvent with charged pigment particles dispersed therein is enclosed between the two electrode plates. An electrophoretic fluid may have one type of charged pigment particles dispersed in a solvent or solvent mixture of a contrasting color. In this case, when a voltage difference is imposed between the two electrode plates, the pigment particles migrate by attraction to the plate of polarity opposite that of the pigment particles. Thus, the color showing at the transparent plate can be either the color of the solvent or the color of the pigment particles. Reversal of plate polarity will cause the particles to migrate to the opposite plate, thereby reversing the color. Alternatively, an electrophoretic fluid may have two types of pigment particles of contrasting colors and carrying opposite charges and the two types of pigment particles are dispersed in a clear solvent or solvent mixture. In this case, when a voltage difference is imposed between the two electrode plates, the two types of pigment particles would move to opposite ends (top or bottom) in a display cell. Thus, one of the colors of the two types of the pigment particles would be seen at the viewing side of the display cell.

Many commercial electrophoretic media essentially display only two colors, with a gradient between the black and white extremes, known as "grayscale." Such electrophoretic media either use a single type of electrophoretic particle having a first color in a colored fluid having a second, different color (in which case, the first color is displayed when the particles lie adjacent the viewing surface of the display and the second color is displayed when the particles are spaced from the viewing surface), or first and second types of electrophoretic particles having differing first and second colors in an uncolored fluid. In the latter case, the first color is displayed when the first type of particles lie adjacent the viewing surface of the display and the second color is displayed when the second type of particles lie adjacent the viewing surface). Typically the two colors are black and white.

If a full color display is desired, a color filter array may be deposited over the viewing surface of the monochrome (black and white) display. Displays with color filter arrays rely on area sharing and color blending to create color stimuli. The available display area is shared between three or four primary colors such as red/green/blue (RGB) or red/green/blue/white (RGBW), and the filters can be arranged in one-dimensional (stripe) or two-dimensional (2×2) repeat patterns. Other choices of primary colors or more than three primaries are also known in the art. The three (in the case of RGB displays) or four (in the case of RGBW displays) sub-pixels are chosen small enough so that at the intended viewing distance they visually blend together to a single pixel with a uniform color stimulus ('color blending'). The inherent disadvantage of area sharing is that the colorants are always present, and colors can only be modulated by switching the corresponding pixels of the underlying monochrome display to white or black (switching the corresponding primary colors on or off). For example, in an ideal RGBW display, each of the red, green, blue and white primaries occupy one fourth of the display area (one sub-pixel out of four), with the white sub-pixel being as bright as the underlying monochrome display white, and each of the colored sub-pixels being no lighter than one third of the monochrome display white. The brightness of the white color shown by the display as a whole cannot be more than one half of the brightness of the white sub-pixel (white areas of the display are produced by displaying the one white sub-pixel out of each four, plus each colored sub-pixel in its colored form being equivalent to one third of a white sub-pixel, so the three colored sub-pixels combined contribute no more than the one white sub-pixel). The brightness and saturation of colors is lowered by area-sharing with color pixels switched to black. Area sharing is especially problematic when mixing yellow because it is lighter than any other color of equal brightness, and saturated yellow is almost as bright as white. Switching the blue pixels (one fourth of the display area) to black makes the yellow too dark.

Although seemingly simple, electrophoretic media and electrophoretic devices display complex behaviors. For instance, it has been discovered that simple "on/off" voltage pulses are insufficient to achieve high-quality text in electronic readers. Rather, complicated "waveforms" are needed to drive the particles between states and to assure that the new displayed text does not retain a memory of the previous text, i.e., a "ghost." See, for example, U.S. Patent Application No. 20150213765. Compounded with the complexities of the electric fields, the internal phase, i.e., the mixture of particles (pigment) and fluid, can exhibit unexpected behavior due to interactions between charged species and the surrounding environment (such as an encapsulation medium) upon the application of an electric field. Additionally, unexpected behaviors may result from impurities in the fluid, pigments, or encapsulation medium. Accordingly, it is difficult to predict how an electrophoretic display will respond to variations in the internal phase composition.

SUMMARY OF INVENTION

The invention includes high-performance electrophoretic media formulations. The improved performance results from the inclusion of a novel family of polyol additives, detailed below. In particular, the invention includes electrophoretic media comprising (a) a non-polar fluid, (b) a plurality of first charged particles dispersed in the non-polar fluid, and (c) an additive of Formula I:

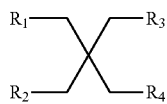

FORMULA I wherein $R_1$, $R_2$, $R_3$, and $R_4$ are independently selected from —OH, —$(CH_2)_m$OH, —$(OCH_2CH_2)_n$OH, —$(OCH_2CHCH_3)_q$OH, —$OCOR_5$, —$(CH_2)_rOCOR_5$, —$(OCH_2CH_2)_tOCOR_5$, and —$(OCH_2CHCH_3)_uOCOR_5$, wherein each $R_5$ is independently a $C_5$-$C_{36}$ branched or unbranched alkane, fluoroalkane, or polyalkylsiloxane, and wherein m, n, q, r, t, and u are independently integers from 1 to 30, and wherein at least one of $R_1$, $R_2$, $R_3$, or $R_4$ is —$OCOR_5$, —$(CH_2)_rOCOR_5$, —$(OCH_2CH_2)_tOCOR_5$, or —$(OCH_2CHCH_3)_uOCOR_5$. In some embodiments, $R_5$ is a $C_{10}$-$C_{20}$ branched or unbranched alkane, fluoroalkane, or polyalkylsiloxane, saturated or unsaturated.

The electrophoretic medium of the invention may include additional types of particles in addition to first charged particles. For example, the electrophoretic medium may include second, third, fourth, fifth or sixth, types of charges particles. The particles may vary in charge, density, hydrophobicity and/or zeta potential. The particles may have different colors, such as magenta, red, orange, yellow, green, cyan, blue, violet, black, and white. The particles may be colorless or transparent. The electrophoretic medium may additionally include surfactants, such as ionic surfactants, i.e., surfactants having a quaternary amine headgroup.

The electrophoretic medium of the invention may be encapsulated, for example in a microcell or a protein coacervate, as discussed in the Background section. In addition, electrophoretic media of the invention can be dispersed in a polymer matrix. The encapsulated or polymer-dispersed electrophoretic media may be incorporated into a front plane laminate (FPL) and/or electro-optic displays as discussed in the Background. Such materials can be used to create electrophoretic image displays (EPID), signs, or architectural materials that will change appearance upon receipt of a signal.

In another aspect, the invention provides an additive of Formula II:

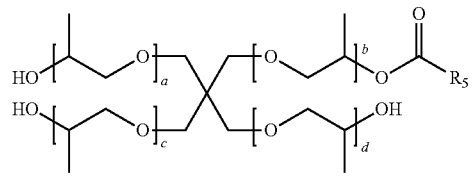

FORMULA II wherein a, b, c, and d are independently integers from 0-20, wherein at least one of a, b, c, and d is 1 or greater, and wherein $R_5$ is a $C_5$-$C_{36}$ branched or unbranched alkane, fluoroalkane, or polyalkylsiloxane. In some embodiments, $R_5$ is a $C_{10}$-$C_{20}$ saturated or unsaturated, branched or unbranched alkane, fluoroalkane, or polyalkylsiloxane. In some embodiments, $R_5$ is a stearate. In some embodiments, a, c, and d are 1 while b is 2.

In yet another aspect, the invention provides an additive of Formula III:

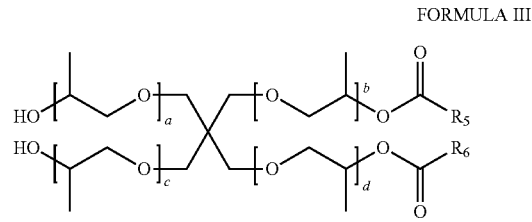

FORMULA III wherein a, b, c, and d are independently integers from 0-20, wherein at least one of a, b, c, and d is 1 or greater, and wherein $R_5$ is a $C_5$-$C_{36}$ branched or unbranched alkane, fluoroalkane, or polyalkylsiloxane. In some embodiments, $R_5$ or $R_6$ is a $C_{10}$-$C_{20}$ saturated or unsaturated, branched or unbranched alkane, fluoroalkane, or polyalkylsiloxane. In some embodiments, $R_5$ or $R_6$ is a stearate. In some embodiments, $R_5$ is a stearate. In some embodiments, a and c are 1 while b and d are 2.

DETAILED DESCRIPTION

The performance of various types of electrophoretic media can be improved with by including the additives described herein. For example, additives of the invention can improve the contrast between light (on) and dark (off) states for a variety of pigments used in electrophoretic displays. Additionally, the additives decrease the incidence and intensity of leftover images after a display has been switched between images, a phenomenon known as "ghosting."

In general, additives of the invention are of the type shown in Formula I, below

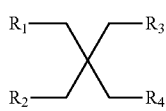

FORMULA I where $R_1$, $R_2$, $R_3$, and $R_4$ are independently selected from —OH, —$(CH_2)_m$OH, —$(OCH_2CH_2)_n$OH, —$(OCH_2CHCH_3)_q$OH, —$OCOR_5$, —$(CH_2)_rOCOR_5$, —$(OCH_2CH_2)_tOCOR_5$, and —$(OCH_2CHCH_3)_uOCOR_5$, wherein each $R_5$ is independently a $C_5$-$C_{36}$ branched or unbranched alkane, fluoroalkane, or polyalkylsiloxane, and wherein m, n, q, r, t, and u are independently integers from 1 to 30, and wherein at least one of $R_1$, $R_2$, $R_3$, or $R_4$ is —$OCOR_5$, —$(CH_2)_rOCOR_5$, —$(OCH_2CH_2)_tOCOR_5$, or —$(OCH_2CHCH_3)_uOCOR_5$. For example, the additive may be of Formula II:

FORMULA II

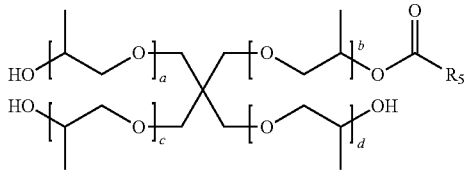

wherein a, b, c, and d are independently integers from 0-20, wherein at least one of a, b, c, and d is 1 or greater, and wherein $R_5$ is a $C_5$-$C_{36}$ branched or unbranched alkane, fluoroalkane, or polyalkylsiloxane. Alternatively, the additive can be of Formula III:

FORMULA III

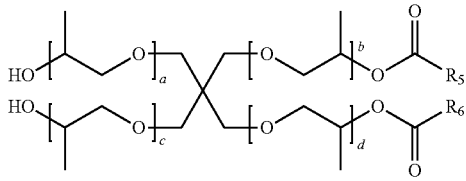

wherein a, b, c, and d are independently integers from 0-20, wherein at least one of a, b, c, and d is 1 or greater, and wherein $R_5$ is a $C_5$-$C_{36}$ branched or unbranched alkane, fluoroalkane, or polyalkylsiloxane.

The additives can be synthesized by esterifying branched polyols and fatty acids such as pentaerythritol propoxylate (5/4 PO/OH) and stearic acid. The fatty acids may be saturated or unsaturated, branched or unbranched. In some embodiments, the fatty acids are perfluorinated, or partially fluorinated. In some embodiments, the branched polyol will include oligomers of polypropylene oxide or polyethylene oxide. Many suitable polyols are available from commercial suppliers, such as Sigma-Aldrich.

Additives of the invention can be used with electrophoretic media that include functionalized pigments in an organic solvent. The media may be incorporated into displays, or into front plane laminates or inverted front plane laminates that are coupled to a backplane to make a display. Electrophoretic media of the invention, i.e., including additives of the invention, may include only black and white pigments, i.e., for use in black/white displays. Electrophoretic media of the invention may also be used in colors displays, i.e., including, for example, three, four, five, six, seven, or eight different types of particles. For examples, a display may be constructed where the particles include black, white, and red or black, white, and yellow. Alternatively, the display may include red, green, and blue particles, or cyan, magenta, and yellow particles, or red, green, blue, and yellow particles, or red, green, blue, white, and black particles, or cyan, yellow, magenta, green, white, and black particles.

The additives may be added to an electrophoretic medium at a concentration of greater than 1 g of additive for every 2.5 kg of charged particles, e.g., first charged particles. For example, the additive to charged particle ratio may be 1:2500 (wt/wt), e.g., 1:2000 (wt/wt), e.g., 1:1500 (wt/wt), e.g., 1:1000 (wt/wt), e.g., 1:500 (wt/wt), e.g., 1:250 (wt/wt), e.g., 1:200 (wt/wt), e.g., 1:150 (wt/wt), e.g., 1:100 (wt/wt), e.g., 1:50 (wt/wt), e.g., 1:25 (wt/wt), e.g., 1:10 (wt/wt), e.g., 1:5 (wt/wt). For example, the additive may be present at a ratio of 1:2000 (wt/wt) to 1:5 (wt/wt) with respect to the first charged particles. The additive may have an average molecular weight of greater than 100 grams/mole, e.g., greater than 400 grams/mole, e.g., greater than 500 grams/mole, e.g., greater than 1,000 grams/mole, e.g., greater than 2,000 grams/mole, e.g., greater than 5,000 grams/mole, e.g., greater than 10,000 grams/mole, e.g., greater than 15,000 grams/mole, e.g., greater than 10,000 grams/mole, e.g., greater than 20,000 grams/mole.

The term gray state is used herein in its conventional meaning in the imaging art to refer to a state intermediate two extreme optical states of a pixel, and does not necessarily imply a black-white transition between these two extreme states. For example, several of the E Ink patents and published applications referred to below describe electrophoretic displays in which the extreme states are white and deep blue, so that an intermediate gray state would actually be pale blue. Indeed, as already mentioned, the change in optical state may not be a color change at all. The terms black and white may be used hereinafter to refer to the two extreme optical states of a display, and should be understood as normally including extreme optical states which are not strictly black and white, for example the aforementioned white and dark blue states.

The terms bistable and bistability are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element. It is shown in U.S. Pat. No. 7,170,670 that some particle-based electrophoretic displays capable of gray scale are stable not only in their extreme black and white states but also in their intermediate gray states, and the same is true of some other types of electro-optic displays. This type of display is properly called multi-stable rather than bistable, although for convenience the term bistable may be used herein to cover both bistable and multi-stable displays.

Many of the aforementioned patents and applications recognize that the walls surrounding the discrete microcapsules in an encapsulated electrophoretic medium could be replaced by a continuous phase, thus producing a so-called polymer-dispersed electrophoretic display, in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, U.S. Pat. No. 6,866,760. Accordingly, for purposes of the present application, such polymer-dispersed electrophoretic media are regarded as sub-species of encapsulated electrophoretic media.

A related type of electrophoretic display is a so-called microcell electrophoretic display. In a microcell electrophoretic display, the charged particles and the fluid are not encapsulated within microcapsules but instead are retained within a plurality of cavities formed within a carrier medium, typically a polymeric film. See, for example, U.S. Pat. Nos. 6,672,921 and 6,788,449, both assigned to Sipix Imaging, Inc.

As noted above, electrophoretic media require the presence of a fluid. In most prior art electrophoretic media, this fluid is a liquid, but electrophoretic media can be produced using gaseous fluids; see, for example, Kitamura, T., et al., Electrical toner movement for electronic paper-like display, IDW Japan, 2001, Paper HCS1-1, and Yamaguchi, Y., et al., Toner display using insulative particles charged triboelectrically, IDW Japan, 2001, Paper AMD4-4). See also U.S. Pat. Nos. 7,321,459 and 7,236,291. Such gas-based electrophoretic media appear to be susceptible to the same types of problems due to particle settling as liquid-based electrophoretic media, when the media are used in an orientation which permits such settling, for example in a sign where the medium is disposed in a vertical plane. Indeed, particle settling appears to be a more serious problem in gas-based electrophoretic media than in liquid-based ones, since the lower viscosity of gaseous suspending fluids as compared with liquid ones allows more rapid settling of the electrophoretic particles.

An encapsulated electrophoretic display typically does not suffer from the clustering and settling failure mode of traditional electrophoretic devices and provides further advantages, such as the ability to print or coat the display on a wide variety of flexible and rigid substrates. (Use of the word printing is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; electrophoretic deposition (See U.S. Pat. No. 7,339,715); and other similar techniques.) Thus, the resulting display can be flexible. Further, because the display medium can be printed (using a variety of methods), the display itself can be made inexpensively.

The aforementioned U.S. Pat. No. 6,982,178 describes a method of assembling electrophoretic displays (including an encapsulated electrophoretic display). Essentially, this patent describes a so-called front plane laminate (FPL) which comprises, in order, a light-transmissive electrically-conductive layer; a layer of a solid electro-optic medium in electrical contact with the electrically-conductive layer; an adhesive layer; and a release sheet. Typically, the light-transmissive electrically-conductive layer will be carried on a light-transmissive substrate, which is preferably flexible, in the sense that the substrate can be manually wrapped around a drum (say) 10 inches (254 mm) in diameter without permanent deformation. The term light-transmissive is used in this patent and herein to mean that the layer thus designated transmits sufficient light to enable an observer, looking through that layer, to observe the change in display states of the electro-optic medium, which will normally be viewed through the electrically-conductive layer and adjacent substrate (if present); in cases where the electro-optic medium displays a change in reflectivity at non-visible wavelengths, the term light-transmissive should of course be interpreted to refer to transmission of the relevant non-visible wavelengths. The substrate will typically be a polymeric film, and will normally have a thickness in the range of about 1 to about 25 mil (25 to 634 µm), preferably about 2 to about 10 mil (51 to 254 µm). The electrically-conductive layer is conveniently a thin metal or metal oxide layer of, for example, aluminum or indium tin oxide (ITO), or may be a conductive polymer. Poly(ethylene terephthalate) (PET) films coated with aluminum or ITO are available commercially, for example as aluminized Mylar (Mylar is a Registered Trade Mark) from E.I. du Pont de Nemours & Company, Wilmington Del., and such commercial materials may be used with good results in the front plane laminate.

Assembly of an electro-optic display using such a front plane laminate may be effected by removing the release sheet from the front plane laminate and contacting the adhesive layer with the backplane under conditions effective to cause the adhesive layer to adhere to the backplane, thereby securing the adhesive layer, layer of electro-optic medium and electrically-conductive layer to the backplane. This process is well-adapted to mass production since the front plane laminate may be mass produced, typically using roll-to-roll coating techniques, and then cut into pieces of any size needed for use with specific backplanes.

In addition to the additives of the invention, electrophoretic media may also include charge control agents (CCAs). For example, pigment particles may be functionalized or surface coated with charged or chargeable groups. The CCAs may be absorbed into the particles, they may be covalently bound to the surface of the particles, and they may exist in a charge complex, or be loosely associated via van der Waals forces. Charge control agents often charge the particles by poorly understood and uncontrolled processes, and can lead to undesirably high conductivity of the electrophoretic medium. Also, because the charge control agent is only physically adsorbed on to the particles and is not bound thereto, changes in conditions may cause partial or complete desorption of the charge control agent from the particles, with consequent undesirable changes in the electrophoretic characteristics of the particles. The desorbed charge control agent might resorb on to other surfaces within the electrophoretic medium, and such resorption has the potential for causing additional problems.

Charge control agents comprising a quaternary amine and an unsaturated polymeric tail comprising monomers of at least 10 carbon atoms in length are preferred. Quaternary amines comprise a quaternary ammonium cation $[NR_1R_2R_3R_4]^+$ bonded to an organic molecule, for example an alkyl group or an aryl group. Quaternary amine charge control agents typically include a long non-polar tail attached to the charged ammonium cation, such as the families of fatty acid quaternary amines offered by Akzo Nobel under the tradenames ARQUAD. The quaternary amine charge control agents may be purchased in a purified form, or the charge control agents may be purchased as a reaction product that has formed a quaternary amine charge control agent. For example, SOLSPERSE 17000 (Lubrizol Corporation), may be purchased as a reaction product of 12-hydroxy-octadecanoic acid homopolymer with N,N-dimethyl-1,3-propanediamine and methylbisulfate. Other useful ionic charge control agents include, but are not limited to, sodium dodecylbenzenesulfonate, metal soap, polybutene succinimide, maleic anhydride copolymers, vinylpyridine copolymers, vinylpyrrolidone copolymer, (meth)acrylic acid copolymers or N,N-dimethylaminoethyl(meth)acrylate copolymers), Alcolec LV30 (soy lecithin), Petrostep B100 (petroleum sulfonate) or B70 (barium sulfonate), OLOA 11000 (succinimide ashless dispersant), OLOA 1200 (polyisobutylene succinimides), Unithox 750 (ethoxylates), Petronate L (sodium sulfonate), Disper BYK 101, 2095, 185, 116, 9077 & 220 and ANTITERRA series.

The charge control agents may be added to the electrophoretic medium at a concentration of greater than 1 g of charge control agent for every 100 g of charged particles. For example, the charge control agent to charged particle ratio may be 1:30 (wt/wt), e.g., 1:25 (wt/wt), e.g., 1:20 (wt/wt). The charge control agents may have an average molecular weight of greater than 12,000 grams/mole, e.g., greater than 13,000 grams/mole, e.g., greater than 14,000 grams/mole, e.g., greater than 15,000 grams/mole, e.g., greater than 16,000 grams/mole, e.g., greater than 17,000 grams/mole, e.g., greater than 18,000 grams/mole, e.g., greater than 19,000 grams/mole, e.g., greater than 20,000 grams/mole, e.g., greater than 21,000 grams/mole. For example, the average molecular weight of the charge control agent may be between 14,000 grams/mole and 22,000 grams/mole, e.g., between 15,000 grams/mole and 20,000 grams/mole. In some embodiments, the charge control agents have an average molecular weight of about 19,000 grams/mole.

Additional charge control agents may be used, with or without charged groups in polymer coatings, to provide good electrophoretic mobility to the electrophoretic particles. Stabilizers may be used to prevent agglomeration of the electrophoretic particles, as well as prevent the electrophoretic particles from irreversibly depositing onto the capsule wall. Either component can be constructed from materials across a wide range of molecular weights (low molecular weight, oligomeric, or polymeric), and may be a single pure compound or a mixture. An optional charge control agent or charge director may be used. These constituents typically consist of low molecular weight surfactants, polymeric agents, or blends of one or more components and serve to stabilize or otherwise modify the sign and/or magnitude of the charge on the electrophoretic particles. Additional pigment properties which may be relevant are the particle size distribution, the chemical composition, and the lightfastness.

As already indicated, the suspending fluid containing the particles should be chosen based on properties such as density, refractive index, and solubility. A preferred suspending fluid has a low dielectric constant (about 2), high volume resistivity (about $10^{15}$ ohm-cm), low viscosity (less than 5 centistokes ("cst")), low toxicity and environmental impact, low water solubility (less than 10 parts per million ("ppm")), high specific gravity (greater than 1.5), a high boiling point (greater than 90° C.), and a low refractive index (less than 1.2).

The choice of non-polar fluid may be based on concerns of chemical inertness, density matching to the electrophoretic particle, or chemical compatibility with both the electrophoretic particle and bounding capsule (in the case of encapsulated electrophoretic displays). The viscosity of the fluid should be low when movement of the particles is desired. The refractive index of the suspending fluid may also be substantially matched to that of the particles. As used herein, the refractive index of a suspending fluid "is substantially matched" to that of a particle if the difference between their respective refractive indices is between about zero and about 0.3, and is preferably between about 0.05 and about 0.2.

Non-polar organic solvents, such as halogenated organic solvents, saturated linear or branched hydrocarbons, silicone oils, and low molecular weight halogen-containing polymers are some useful non-polar fluids. The non-polar fluid may comprise a single fluid. The non-polar fluid will, however, often be a blend of more than one fluid in order to tune its chemical and physical properties. Furthermore, the non-polar fluid may contain additional surface modifiers to modify the surface energy or charge of the electrophoretic particle or bounding capsule. Reactants or solvents for the microencapsulation process (oil soluble monomers, for example) can also be contained in the suspending fluid. Additional charge control agents can also be added to the suspending fluid.

Useful organic solvents include, but are not limited to, epoxides, such as decane epoxide and dodecane epoxide; vinyl ethers, such as cyclohexyl vinyl ether and Decave (Registered Trade Mark of International Flavors & Fragrances, Inc., New York, N.Y.); and aromatic hydrocarbons, such as toluene and naphthalene. Useful halogenated organic solvents include, but are not limited to, tetrafluorodibromoethylene, tetrachloroethylene, trifluorochloroethylene, 1,2,4-trichlorobenzene and carbon tetrachloride. These materials have high densities. Useful hydrocarbons include, but are not limited to, dodecane, tetradecane, the aliphatic hydrocarbons in the Isopar (Registered Trade Mark) series (Exxon, Houston, Tex.), Norpar (Registered Trade Mark) (a series of normal paraffinic liquids), Shell-Sol (Registered Trade Mark) (Shell, Houston, Tex.), and Sol-Trol (Registered Trade Mark) (Shell), naphtha, and other petroleum solvents. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials usually have low densities. Useful low molecular weight halogen-containing polymers include, but are not limited to, poly(chlorotrifluoroethylene) polymer (Halogenated Hydrocarbon Inc., River Edge, N.J.), Galden (Registered Trade Mark) (a perfluorinated ether from Ausimont, Morristown, N.J.), or Krytox (Registered Trade Mark) from du Pont (Wilmington, Del.). In a preferred embodiment, the suspending fluid is a poly (chlorotrifluoroethylene) polymer. In a particularly preferred embodiment, this polymer has a degree of polymerization from about 2 to about 10. Many of the above materials are available in a range of viscosities, densities, and boiling points.

In some embodiments, the non-polar fluid will include an optically absorbing dye. This dye must be soluble in the fluid, but will generally be insoluble in the other components of the capsule. There is much flexibility in the choice of dye material. The dye can be a pure compound, or blends of dyes to achieve a particular color, including black. The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

A number of dyes already known to those skilled in the art of electrophoretic displays will prove useful. Useful azo dyes include, but are not limited to: the Oil Red dyes, and the Sudan Red and Sudan Black series of dyes. Useful anthraquinone dyes include, but are not limited to: the Oil Blue dyes, and the Macrolex Blue series of dyes. Useful triphenylmethane dyes include, but are not limited to, Michler's hydrol, Malachite Green, Crystal Violet, and Auramine O. The core particle may be of an inorganic pigment such as $TiO_2$, $ZrO_2$, ZnO, $Al_2O_3$, CI pigment black 26 or 28 or the like (e.g., manganese ferrite black spinel or copper chromite black spinel), or an organic pigment such as phthalocyanine blue, phthalocyanine green, diarylide yellow, diarylide AAOT yellow, and quinacridone, azo, rhodamine, perylene pigment series from Sun Chemical, Hansa yellow G particles from Kanto Chemical, and Carbon Lampblack from Fisher or the like.

Particle dispersion stabilizers may also be added to prevent particle flocculation or attachment to the capsule walls. For the typical high resistivity liquids used as suspending fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

If a bistable electrophoretic medium is desired, it may be desirable to include in the suspending fluid a polymer having a number average molecular weight in excess of about 20,000, this polymer being essentially non-absorbing on the electrophoretic particles; poly(isobutylene) is a preferred polymer for this purpose. See U.S. Pat. No. 7,170,670, the entire disclosure of which is herein incorporated by reference.

Encapsulation of the internal phase may be accomplished in a number of different ways. Numerous suitable procedures for microencapsulation are detailed in both Microencapsulation, Processes and Applications, (I. E. Vandegaer, ed.), Plenum Press, New York, N.Y. (1974) and Gutcho, Microcapsules and Microencapsulation Techniques, Noyes Data Corp., Park Ridge, N.J. (1976). The processes fall into several general categories, all of which can be applied to the present invention: interfacial polymerization, in situ polymerization, physical processes, such as coextrusion and other phase separation processes, in-liquid curing, and simple/complex coacervation.

Numerous materials and processes should prove useful in formulating displays of the present invention. Useful materials for simple coacervation processes to form the capsule include, but are not limited to, gelatin, poly(vinyl alcohol), poly(vinyl acetate), and cellulosic derivatives, such as, for example, carboxymethylcellulose. Useful materials for complex coacervation processes include, but are not limited to, gelatin, acacia, carageenan, carboxymethylcellulose, hydrolyzed styrene anhydride copolymers, agar, alginate, casein, albumin, methyl vinyl ether co-maleic anhydride, and cellulose phthalate. Useful materials for phase separation processes include, but are not limited to, polystyrene, poly (methyl methacrylate) (PMMA), poly(ethyl methacrylate), poly(butyl methacrylate), ethyl cellulose, poly(vinylpyridine), and polyacrylonitrile. Useful materials for in situ polymerization processes include, but are not limited to, polyhydroxyamides, with aldehydes, melamine, or urea and formaldehyde; water-soluble oligomers of the condensate of melamine, or urea and formaldehyde; and vinyl monomers, such as, for example, styrene, methyl methacrylate (MMA) and acrylonitrile. Finally, useful materials for interfacial polymerization processes include, but are not limited to, diacyl chlorides, such as, for example, sebacoyl, adipoyl, and di- or poly-amines or alcohols, and isocyanates. Useful emulsion polymerization materials may include, but are not limited to, styrene, vinyl acetate, acrylic acid, butyl acrylate, t-butyl acrylate, methyl methacrylate, and butyl methacrylate.

Capsules produced may be dispersed into a curable carrier, resulting in an ink which may be printed or coated on large and arbitrarily shaped or curved surfaces using conventional printing and coating techniques.

In the context of the present invention, one skilled in the art will select an encapsulation procedure and wall material based on the desired capsule properties. These properties include the distribution of capsule radii; electrical, mechanical, diffusion, and optical properties of the capsule wall; and chemical compatibility with the internal phase of the capsule.

The capsule wall generally has a high electrical resistivity. Although it is possible to use walls with relatively low resistivities, this may limit performance in requiring relatively higher addressing voltages. The capsule wall should also be mechanically strong (although if the finished capsule powder is to be dispersed in a curable polymeric binder for coating, mechanical strength is not as critical). The capsule wall should generally not be porous. If, however, it is desired to use an encapsulation procedure that produces porous capsules, these can be overcoated in a post-processing step (i.e., a second encapsulation). Moreover, if the capsules are to be dispersed in a curable binder, the binder will serve to close the pores. The capsule walls should be optically clear. The wall material may, however, be chosen to match the refractive index of the internal phase of the capsule (i.e., the suspending fluid) or a binder in which the capsules are to be dispersed. For some applications (e.g., interposition between two fixed electrodes), monodispersed capsule radii are desirable.

An encapsulation technique that is suited to the present invention involves a polymerization between urea and formaldehyde in an aqueous phase of an oil/water emulsion in the presence of a negatively charged, carboxyl-substituted, linear hydrocarbon polyelectrolyte material. The resulting capsule wall is a urea/formaldehyde copolymer, which discretely encloses the internal phase. The capsule is clear, mechanically strong, and has good resistivity properties.

The related technique of in situ polymerization utilizes an oil/water emulsion, which is formed by dispersing the electrophoretic fluid (i.e., the dielectric liquid containing a suspension of the pigment particles) in an aqueous environment. The monomers polymerize to form a polymer with higher affinity for the internal phase than for the aqueous phase, thus condensing around the emulsified oily droplets. In one in situ polymerization process, urea and formaldehyde condense in the presence of poly(acrylic acid) (see, e.g., U.S. Pat. No. 4,001,140). In other processes, described in U.S. Pat. No. 4,273,672, any of a variety of cross-linking agents borne in aqueous solution is deposited around microscopic oil droplets. Such cross-linking agents include aldehydes, especially formaldehyde, glyoxal, or glutaraldehyde; alum; zirconium salts; and polyisocyanates.

The coacervation approach also utilizes an oil/water emulsion. One or more colloids are coacervated (i.e., agglomerated) out of the aqueous phase and deposited as shells around the oily droplets through control of temperature, pH and/or relative concentrations, thereby creating the microcapsule. Materials suitable for coacervation include gelatins and gum arabic. See, e.g., U.S. Pat. No. 2,800,457.

The interfacial polymerization approach relies on the presence of an oil-soluble monomer in the electrophoretic composition, which once again is present as an emulsion in an aqueous phase. The monomers in the minute hydrophobic droplets react with a monomer introduced into the aqueous phase, polymerizing at the interface between the droplets and the surrounding aqueous medium and forming shells around the droplets. Although the resulting walls are relatively thin and may be permeable, this process does not require the elevated temperatures characteristic of some other processes, and therefore affords greater flexibility in terms of choosing the dielectric liquid.

Additional materials may be added to encapsulated medium to improve the construction of an electrophoretic display. For example, coating aids can be used to improve the uniformity and quality of the coated or printed electrophoretic ink material. Wetting agents may be added to adjust the interfacial tension at the coating/substrate interface and to adjust the liquid/air surface tension. Wetting agents include, but are not limited to, anionic and cationic surfactants, and nonionic species, such as silicone or fluoropolymer-based materials. Dispersing agents may be used to modify the interfacial tension between the capsules and binder, providing control over flocculation and particle settling.

In other embodiments, the electrophoretic medium may be contained in microfabricated cells, i.e., microcells, such as fabricated by E Ink under the tradename MICROCUP. Once the microcells are filled with the electrophoretic medium, the microcells are sealed, an electrode (or an electrode array) is affixed to the microcells, and the filled microcells are driven with electric fields to create a display.

For example, as described in U.S. Pat. No. 6,930,818, a male mold may be used to imprint a conductive substrate, upon which is formed a transparent conductor film. A layer of a thermoplastic or thermoset precursor is then coated on the conductor film. The thermoplastic or thermoset precursor layer is embossed at a temperature higher than the glass transition temperature of the thermoplastic or thermoset precursor layer by the male mold in the form of a roller, plate or belt. Once formed, the mold is released during or after the precursor layer is hardened to reveal an array of microcells. The hardening of the precursor layer may be accomplished by cooling, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer.

The thermoplastic or thermoset precursor for the preparation of the microcells may be multifunctional acrylate or methacrylate, vinylether, epoxide and their oligomers, polymers and the like. A crosslinkable oligomer imparting flexibility, such as urethane acrylate or polyester acrylate, is usually also added to improve the flexure resistance of the embossed micro-cups. The composition may contain polymer, oligomer, monomer and additives or only oligomer, monomer and additives.

In general, the microcells can be of any shape, and their sizes and shapes may vary. The microcells may be of substantially uniform size and shape in one system. However, in order to maximize the optical effect, microcells having a mixture of different shapes and sizes may be produced. For example, microcells filled with a dispersion of the red color may have a different shape or size from the green microcells or the blue microcells. Furthermore, a pixel may consist of different numbers of microcells of different colors. For example, a pixel may consist of a number of small green microcells, a number of large red microcells, and a number of small blue microcells. It is not necessary to have the same shape and number for the three colors.

The openings of the microcells may be round, square, rectangular, hexagonal, or any other shape. The partition area between the openings is preferably kept small in order to achieve a high color saturation and contrast while maintaining desirable mechanical properties. Consequently the honeycomb-shaped opening is preferred over, for example, the circular opening.

For reflective electrophoretic displays, the dimension of each individual microcell may be in the range of about $10^2$ to about $5 \times 10^5$ $\mu m^2$, preferably from about $10^3$ about $5 \times 10^4$ $\mu m^2$. The depth of the microcells is in the range of about 3 to about 100 microns, preferably from about 10 to about 50 microns. The opening to wall ratio is in the range of from about 0.05 to about 100, preferably from about 0.4 to about 20. The distances of the openings usually are in the range of from about 15 to about 450 microns, preferably from about 25 to about 300 microns from edge to edge of the openings.

Taken together, it will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

EXAMPLES

Example 1—Synthesis of V052 Additive

An additive for improved performance of electrophoretic systems (V052) is

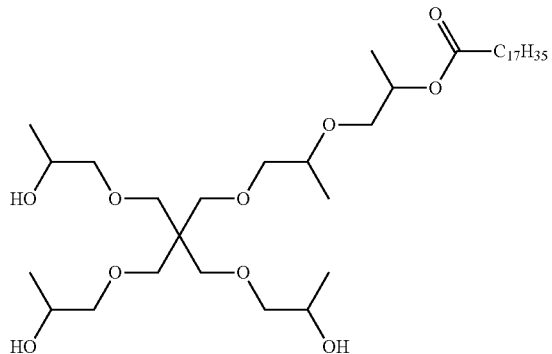

shown in Formula IV.

Formula IV

To synthesize V052, oxalyl chloride (28.0 mL, 1.04 eq) was added dropwise over 1 h to a vigorously stirred suspension of stearic acid (89.0 g, 1 eq) in DCM (300 mL) and DMF (6.0 mL) in a 1 L round bottom flask taking care not to let foaming (due to gas evolution) get out of control. Following the completion of addition, the brown reaction mixture was additionally stirred for 30 min, concentrated on a rotary evaporator and redissolved in DCM (200 mL). In a separate 2 L round bottom flask pentaerythritol propoxylate 5/4 PO/OH (200 g, 1.50 eq.) was dissolved in DCM (0.5 L). TEA (46.0 mL, 1.10 eq) and DMAP (477 mg, 0.01 eq.) were added all-at-once. The stearyl chloride solution was transferred dropwise via a cannula to the resulting stirred solution over 3 h. After allowing the reaction mixture to stir for an additional 2 h, white precipitate (triethylamine hydrochloride) was filtered out and the filtrate was concentrated on a rotary evaporator. Purification by silica gel chromatography (hexanes→7:3 ethyl acetate:hexanes) afforded V052 (115 g, 53%) as a light yellow clear oil that was used directly for addition to electrophoretic particle systems, as described below. This synthetic scheme will result in V052 with a mixture of isomers. All reagents and solvents used in the synthesis were purchased from commercial sources and used without additional purification.

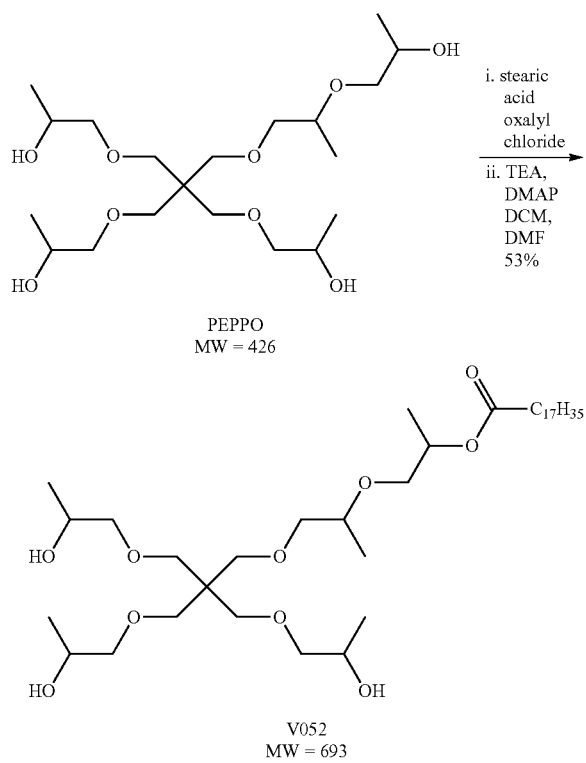

PEPPO
MW = 426 i. stearic acid oxalyl chloride
ii. TEA, DMAP DCM, DMF 53%

V052
MW = 693

Example 2—V052 Additive in Two-Particle System

The V052 additive was added to a two-electrophoretic particle system of the type described in U.S. Patent Publication Nos. 2013/0077155 and 2013/0250400, both of which are incorporated herein by reference in their entireties. A formulation including 1:40 (wt/wt) of V052 to electrophoretic particle was compared to a control medium that contained no additive. The prepared samples were then driven with 3.3 Volt waveforms at 20° C. and 0° C. The displays were evaluated for relative reflectance and color in the light and dark states using an X-rite iOne spectrophotometer with D65 illumination (X-rite, Grand Rapids, Mich.). The data is reported using both CIExyY and CIELAB color space algorithms. The level of ghosting was determined by driving the display between light and dark images and evaluating the amount of residual reflectance when going from light to dark images, and the amount of reduced reflectance when going from dark to light images. In practice, each display was driven between positive and negative checkerboard patterns while the change in L* was measured at several locations, thereby allowing for the collection of many relevant data points in a short amount of time.

As shown in Table 1, the V052 additive improved the white state reflectance by 2.5% and contrast ratio by 12% while additionally reducing ghosting, i.e., the appearance of ghost images after the medium is switched between images. These trends were evident at both 20° C. and 0° C., however the differences between the additive and the controls were more pronounced at low temperature.

TABLE 1

Comparison of two-particle electrophoretic display performance with and without V052 additive.

| Temperature & Voltage | Property | Control | 1:40 V052 |
|---|---|---|---|
| RT At 3.3 V | W (Y) | 43.0 | 45.5 |
| | K (Y) | 1.8 | 1.7 |
| | Contrast | 23.9 | 26.8 |
| | White Ghosting (ΔL*) | 1.7 | 0.6 |
| | Black Ghosting (ΔL*) | 0.6 | 0.4 |
| 0° C. Performance at 3.3 V | W (Y) | 25.7 | 31.8 |
| | K (Y) | 2.7 | 2.1 |
| | Contrast | 9.5 | 14.9 |
| | White Ghosting (ΔL*) | 2.1 | 0.6 |
| | Black Ghosting (ΔL*) | 1.3 | 0.6 |

Example 3—V052 Additive in Three Particle System

The V052 additive was added to a three-electrophoretic particle system of the type described in U.S. Patent Publication No. 2014/0092465, incorporated herein by reference in its entirety. A formulation including 1:200 (wt/wt) of V052 to electrophoretic particle was compared to a control medium that contained no additive. The samples were driven with 15 Volt waveforms at 20° C.

As shown in Table 2, the V052 additive improved the white and dark states, the contrast ratio, tinting, and ghosting of the three-particle system.

TABLE 2

Comparison of three-particle electrophoretic display performance with and without V052 additive.

| Material differences | | Control | 1:200 V052 |
|---|---|---|---|
| White | L* | 66.1 | 73.1 |
| | a* | 2.9 | 1.0 |
| | Y | 35.4 | 45.4 |
| Black | L* | 13.1 | 13.8 |
| | a* | 7.4 | 7.9 |
| | Y | 1.6 | 1.7 |
| W/K Contrast | CR | 22.1 | 26.7 |
| Red | L* | 25.7 | 26.8 |
| | a* | 36.1 | 37.7 |
| White Ghosting | ΔL* | 4.3 | 0.9 |
| | Δa* | 0.9 | 0.5 |
| Black Ghosting | ΔL* | −0.7 | −1.1 |
| | Δa* | −3.0 | −3.5 |

Example 4—Two-Particle System with Pentaerythritol Monostearate

A similar set of experiments were used to evaluate pentaerythritol monostearate as an additive for a two-electrophoretic particle system of the type described in U.S. Patent Publication Nos. 2013/0077155 and 2013/0250400. The structure of pentaerythritol monostearate is shown below.

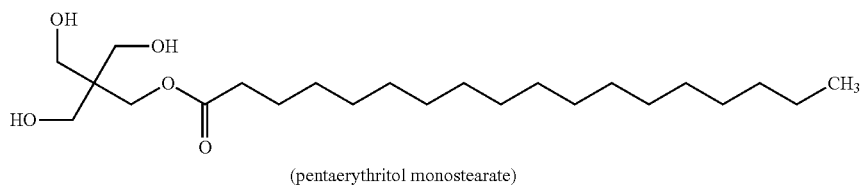 [SMILES: CCCCCCCCCCCCCCCCCC(=O)OCC(CO)(CO)CO]

(pentaerythritol monostearate)

A formulation including 1:200 (wt/wt) of pentaerythritol monostearate (Sigma-Aldrich) to electrophoretic particle was prepared. A control medium that contained no additive was also prepared. The prepared samples were then driven with 5 Volt waveforms at 20° C. and 0° C.

As shown in Table 3, the formulations including pentaerythritol monostearate showed improved whiteness, darkness, contrast ratio, and ghosting. These trends were evident at both 20° C. and 0° C.

TABLE 3

Comparison of two-particle electrophoretic display performance with and without pentaerythritol monostearate.

| Temperature & Voltage | Property | Control | 1:200 PM |
|---|---|---|---|
| RT At 5 V | W (Y) | 47.6 | 49.7 |
| | K (Y) | 1.9 | 1.8 |
| | Contrast | 25.1 | 27.6 |
| | White Ghosting ($\Delta L^*$) | 1.0 | 0.6 |
| | Black Ghosting ($\Delta L^*$) | 1.0 | 0.2 |
| 0° C. Performance at 5 V | W (Y) | 31.9 | 33.0 |
| | K (Y) | 2.5 | 2.2 |
| | CR | 12.8 | 15.1 |
| | White Ghosting ($\Delta L^*$) | 0.5 | 0.7 |
| | Black Ghosting ($\Delta L^*$) | 0.8 | 0.5 |

Example 5—Pentaerythritol Monostearate in Three-Particle System

Pentaerythritol monostearate was added to a three-electrophoretic particle system of the type described in U.S. Patent Publication No. 2014/0092465 to achieve formulations comprising 1:200 (wt/wt) of pentaerythritol monostearate to electrophoretic particle. The three-particle pentaerythritol monostearate formulations were also compared to the 1:200 (wt/wt) V052 formulation described in Example 3. The results are shown in Table 4.

TABLE 4

Comparison of three-particle electrophoretic display performance with pentaerythritol monostearate and V052 additive.

| Material differences | | 1:200 V052 | 1:200 PM |
|---|---|---|---|
| White | L* | 75.1 | 71.1 |
| | a* | −0.4 | −0.4 |
| Black | L* | 12.4 | 13.2 |
| | a* | 4.1 | 4.2 |
| Contrast | | 29.9 | 26.5 |
| Red | L* | 29.5 | 29.3 |
| | a* | 38.1 | 37.7 |
| Ghosting | Red Ghosting GL* | 1.3 | 1.7 |
| | Red Ghosting Ga* | 3.4 | 5.9 |
| | White Ghosting ($\Delta L^*$) | 3.1 | 2.2 |
| | White Ghosting ($\Delta a^*$) | 0.6 | 1.0 |
| | Black Ghosting ($\Delta L^*$) | 0.4 | 0.4 |
| | Black Ghosting ($\Delta a^*$) | 5.9 | 6.5 |

Example 6—3-Hydroxy-2-(Hydroxymethyl)-2-[(Stearoyloxy)Methyl]Propyl Stearate (HPS) in Three-Particle System 3-Hydroxy-2-(hydroxymethyl)-2-[(stearoyloxy)methyl] propyl stearate (HPS) (Sigma-Aldrich) was also added to a three-electrophoretic particle system of the type described in U.S. Patent Publication No. 2014/0092465 to achieve formulations comprising ratios of 1:200 (wt/wt) HPS to electrophoretic particles. The structure of HPS is shown below.

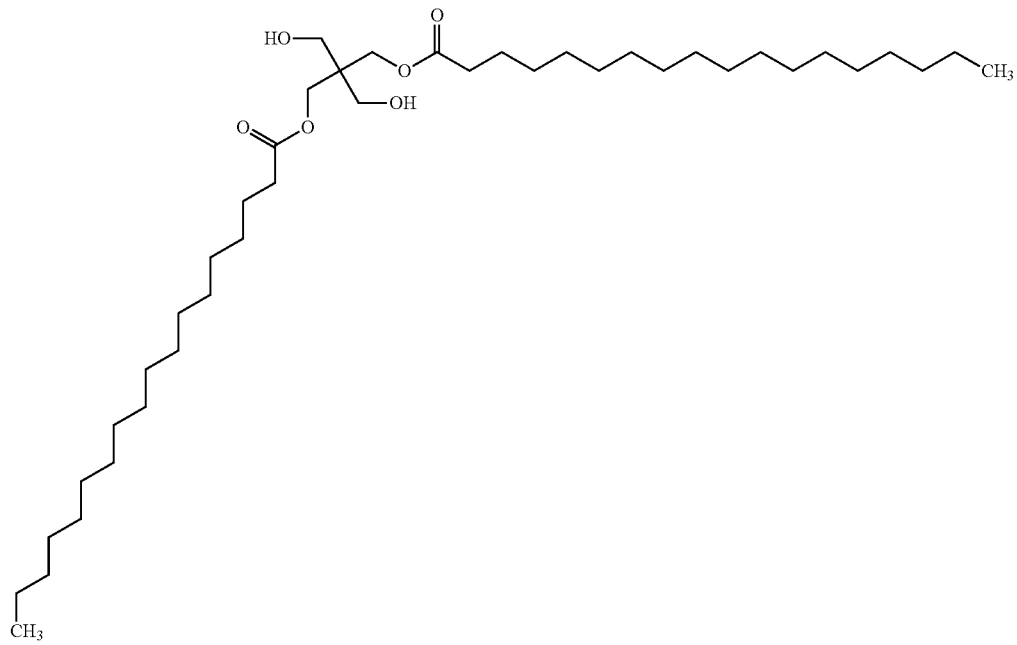 [SMILES: CCCCCCCCCCCCCCCCCC(=O)OCC(CO)(CO)COC(=O)CCCCCCCCCCCCCCCCC]

The three-particle HPS formulations were also compared to the 1:200 (wt/wt) of V052 described in Example 3. The results are shown in Table 5. As shown in Table 5, HPS improves the whiteness, contrast ratio, and ghosting of a three-particle system.

TABLE 5

Comparison of three-particle electrophoretic display performance with 3-Hydroxy-2-(hydroxymethyl)-2-[(stearoyloxy)methyl]propyl stearate (HPS) and V052 additive.

| Material differences | | 1:200 V052 | 1:200 HPS |
|---|---|---|---|
| White | L* | 72.2 | 74.1 |
|  | a* | −0.2 | −0.6 |
| Black | L* | 11.6 | 11.8 |
|  | a* | 5.8 | 5.8 |
| Contrast |  | 32.6 | 34.0 |
| Red | L* | 29.5 | 27.6 |
|  | a* | 38.9 | 37.0 |
| Ghosting | Red Ghosting GL* | 1.4 | 1.6 |
|  | Red Ghosting Ga* | 2.1 | 1.9 |
|  | White Ghosting (ΔL*) | 2.4 | 1.1 |
|  | White Ghosting (Δa*) | 0.4 | 0.2 |
|  | Black Ghosting (ΔL*) | 0.7 | 0.5 |
|  | Black Ghosting (Δa*) | 5.9 | 4.0 |

As indicated above, the present invention provides additives that can be included in electrophoretic media to improve the performance of the media.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

The invention claimed is:

1. An electrophoretic medium comprising:
   (a) a non-polar fluid;
   (b) a plurality of first charged particles dispersed in the non-polar fluid; and
   (c) an additive of Formula I

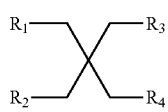

FORMULA I wherein $R_1$, $R_2$, $R_3$, and $R_4$ are independently selected from the group consisting of —OH, —$(CH_2)_m$OH, —$(OCH_2CH_2)_n$OH, —$(OCH_2CHCH_3)_q$OH, —$OCOR_5$, —$(CH_2)_r OCOR_5$, —$(OCH_2CH_2)_t OCOR_5$, and —$(OCH_2CHCH_3)_u OCOR_5$, wherein each $R_5$ is independently a $C_5$-$C_{28}$ branched or unbranched fluoroalkane, and m, n, q, r, t, and u are independently integers from 1 to 30, and wherein at least one of $R_1$, $R_2$, $R_3$, or $R_4$ is —$OCOR_5$, —$(CH_2)_r OCOR_5$, —$(OCH_2CH_2)_t OCOR_5$, or —$(OCH_2CHCH_3)_u OCOR_5$.

2. The electrophoretic medium of claim 1, wherein $R_5$ is a $C_{10}$-$C_{20}$ unbranched fluoroalkane.

3. The electrophoretic medium of claim 1, wherein $R_5$ is $C_{17}F_{35}$.

4. The electrophoretic medium of claim 1, $R_1$, $R_2$, and $R_3$ are —OH, $R_4$ is —$OCOR_5$, and $R_5$ is a $C_5$-$C_{28}$ branched or unbranched fluoroalkane.

5. The electrophoretic medium of claim 4, wherein $R_5$ is $C_{17}F_{35}$.

6. The electrophoretic medium of claim 1, further comprising a plurality of second charged particles dispersed in the non-polar fluid, wherein the first and second charged particles have opposite charges.

7. The electrophoretic medium of claim 1, further comprising an ionic surfactant.

8. The electrophoretic medium of claim 7, wherein the ionic surfactant comprises a quaternary amine.

9. An encapsulated electrophoretic medium comprising the electrophoretic medium of claim 1.

10. The encapsulated electrophoretic medium of claim 9, wherein the electrophoretic medium is encapsulated in a microcell or a protein coacervate.

11. The encapsulated electrophoretic medium of claim 10, wherein the protein coacervate comprises gelatin.

12. The electrophoretic medium of claim 1, wherein the electrophoretic medium is dispersed in a polymer.

13. The electrophoretic medium of claim 1, wherein the first charged particles comprise titania, carbon black, or copper chromite.

14. The electrophoretic medium of claim 1, wherein a ratio of additive to first charged particles is greater than 1:500.

15. The electrophoretic medium of claim 1, wherein the conductivity of the electrophoretic medium is less than 300 pS/m.

16. The electrophoretic medium of claim 1, further comprising a plurality of second charged particles and a plurality of third charged particles dispersed in the nonpolar fluid, wherein the first, the second, or the third charged particles are red, green, blue, cyan, yellow, or magenta.

17. The electrophoretic medium of claim 1, wherein the non-polar fluid comprises $C_6$-$C_{18}$ branched alkanes.

18. The electrophoretic medium of claim 1, wherein the non-polar fluid comprises $C_7$-$C_{10}$ branched alkanes.

19. An additive of Formula II:

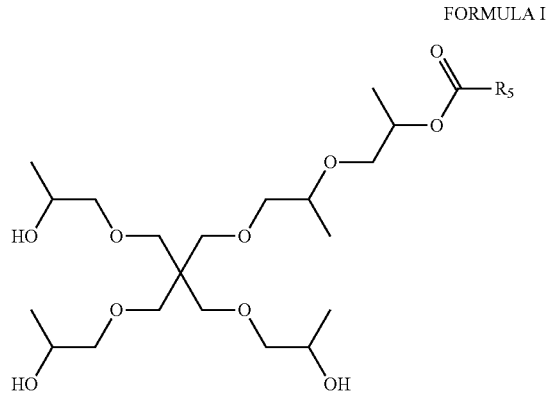

FORMULA II wherein $R_5$ is a $C_5$-$C_{28}$ branched or unbranched alkane or fluoroalkane.

20. The additive of claim 19, wherein $R_5$ is a $C_{10}$-$C_{20}$ unbranched alkane or fluoroalkane.

21. The additive of claim 19, wherein $R_5$ is $C_{17}H_{35}$ or $C_{17}F_{35}$.

22. The additive of claim 19, wherein $R_5$ is a stearate.

23. An additive of Formula III:
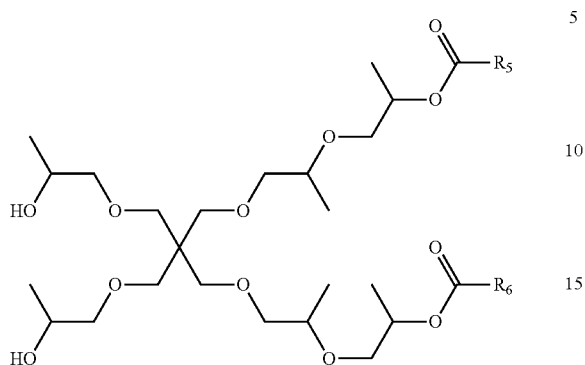
FORMULA III
wherein $R_5$ and $R_6$ are independently $C_5$-$C_{28}$ branched or unbranched alkanes or fluoroalkanes.
24. The additive of claim 23, wherein $R_5$ or $R_6$ is a $C_{10}$-$C_{20}$ unbranched alkane of fluoroalkane.
25. The additive of claim 23, wherein $R_5$ or $R_6$ is $C_{17}H_{35}$ or $C_{17}F_{35}$.
26. The additive of claim 23, wherein $R_5$ or $R_6$ is a stearate.
* * * * *